United States Patent [19]
Shono et al.

[11] Patent Number: 5,698,209
[45] Date of Patent: Dec. 16, 1997

[54] ARTHROPOD REPELLENT COMPOSITION

[75] Inventors: Yoshinori Shono, Sanda; Yoshihiro Takebayashi; Takao Ishiwatari, both of Toyonaka, all of Japan

[73] Assignee: Sumitomo Chemical Company, Limited, Osaka, Japan

[21] Appl. No.: 534,292

[22] Filed: Sep. 27, 1995

[30] Foreign Application Priority Data

Sep. 30, 1994 [JP] Japan .................................. 6-236776
Jun. 20, 1995 [JP] Japan .................................. 7-153251

[51] Int. Cl.$^6$ .................................................. A01N 31/06
[52] U.S. Cl. ................. 424/405; 424/403; 424/DIG. 10; 514/738; 514/919
[58] Field of Search .................................. 514/738, 919; 424/403, 405, DIG. 10

[56] References Cited

U.S. PATENT DOCUMENTS 5,130,136  7/1992  Shono et al. .......................... 424/905

FOREIGN PATENT DOCUMENTS

92/02136  2/1992  WIPO .

OTHER PUBLICATIONS

Patent Abstracts of Japan—JP–B–3–80138.
Patent Abstracts of Japan—JP–A–60–199804.
Patent Abstracts of Japan—JP–A–5–255026.
Patent Abstract of Japan—JP–B–6–10125.
Patent Abstracts of Japan—JP–A–6–183910.

*Primary Examiner*—Neil S. Levy
*Attorney, Agent, or Firm*—Cushman Darby & Cushman IP Group of Pillsbury Madison & Sutro, LLP

[57] ABSTRACT

An arthropod repellent composition containing a monoterpenediol compound selected from carane-3,4-diol- and p-menthane-3,8-diol and a pyrethroid compound selected from phenothrin and permethrin as active ingredients and an inert carrier exhibits an outstandingly high arthropod repellency for a long period of time.

19 Claims, No Drawings

ARTHROPOD REPELLENT COMPOSITION

The present invention relates to an arthropod repellent composition.

It is disclosed in U.S. Pat. No. 5,130,136 that compounds such as carane-3,4-diol, etc. have an arthropod-repelling activity.

Also, it is disclosed in JP-B-3-80138 that compounds such as p-menthane-3,8-diol, etc. have an arthropod-repelling activity.

There is the case, however, where the use of carane-3,4-diol or p-menthane-3,8-diol in a low concentration is insufficient to repel arthropods 100% completely. Moreover, some kinds of arthropods cannot be repelled 100% completely by the use of carane-3,4-diol or p-menthane-3,8-diol.

In repelling arthropods, particularly blood-sucking arthropods such as mosquitoes, black flies, stable flies, etc., the point is to repel these arthropods completely. In other words, even if a 90% repelling activity is maintained for a long time, damage caused by these blood-sucking arthropods cannot be prevented completely, so that the repelling activity cannot be said to be satisfactory in practical use.

That is, how to prevent the damage by blood-sucking arthropods 100% completely for a long time is of great concern in repelling blood-sucking arthropods.

The present inventors have extensively studied to find excellent repellents for various kinds of arthropods, particularly blood-sucking arthropods, thereby solving the above problems, and as a result, have found that compositions containing either carane-3,4-diol or p-menthane-3,8-diol and either phenothrin or permethrin are outstandingly effective to repel these arthropods. The present inventors thus completed the present invention.

That is, the present invention provides a composition containing as active ingredients a monoterpenediol selected from the group consisting of carane-3,4-diol and p-menthane-3,8-diol and a pyrethroid compound selected from the group consisting of phenothrin and permethrin (hereinafter referred to as present composition). The mixing ratio in weight basis of the monoterpenediol (carane-3,4-diol or p-menthane-3,8-diol) and the pyrethroid compound (phenothrin or permethrin) usually falls within the range of from 1:1 to 50:1, preferably 2:1 to 30:1.

Carane-3,4-diol used in the present invention has various stereoisomers, and not only any one of the active isomers among them, but also their mixtures can be used. Among the stereoisomers, however, 1S,3S,4S,6R-carane-3,4-diol, 1S,3R,4R,6R-carane-3,4-diol or carane-3,4-diol mixtures containing these stereoisomers at high mixing ratios are preferred because of their high activity. Particularly, use of 1S,3S,4S,6R-carane-3,4-diol is preferred. As to p-menthane-3,8-diol, similarly, not only any one of its active isomers, but also their mixtures can also be used. Phenothrin [3-phenoxybenzyl chrysanthemate] and permethrin [3-phenoxybenzyl 3,3-dimethyl-2-(2,2-dichlorovinyl) cyclopropanecarboxylate] are compounds which are in practical use as an active ingredient for insecticides. As to these compounds, similarly, not only any one of the active isomers among them, but also their mixtures can also be used.

The target arthropods which can be effectively repelled by the present compositions include blood-sucking insects such as mosquitoes (Culex spp.) represented by Anopheles spp. such as *Anopheles albimanus*, etc., Aedes spp. such as *Aedes aegypti*, *Aedes albopictus*, etc., house mosquitoes (Culex spp.) such as common mosquito (*Culex pipiens pallens*), *Culex tritaeniorphynchus*, etc., black flies (Simuliidae), stable flies (Stomoxyidae), sand flies (Psychodidae), bitting midge, etc.; and Ixodidae such as Amblyomma, Rhipicephalus, Dermacentor, Ixodes, Haemaphysalis, Boophilus, etc.

The present composition is used in various formulations such as liquid formulations (e.g. lotions, aerosols), creams, etc. by usually using a suitable carrier.

The carrier used in formulating into the liquid formulations includes, for example, water, alcohols (e.g. methanol, ethanol, cetyl alcohol), aliphatic hydrocarbons (e.g. petroleum benzine), esters (e.g. ethyl acetate) and the like.

To the liquid formulations may further be added auxiliaries for formulation such as emulsifiers, dispersing agents, spreading agents, wetting agents, suspension-assisting agents, preservatives, propellants, etc., film-forming agents and the like.

The emulsifiers and dispersing agents include, for example, soaps, polyoxyethylene fatty acid alcohol ethers (e.g. polyoxyethylene oleyl ether), polyoxyethylene alkylaryl ethers (e.g. polyoxyethylene nonylphenyl ether), polyoxyethylene fatty acid esters, fatty acid glycerides, sorbitan fatty acid esters (e.g. polyoxyethylene sorbitan monostearate), sulfuric acid esters of higher alcohols, alkylarylsulfonates (e.g sodium dodecylbenzenesulfonate) and the like. The spreading agents and wetting agents include, for example, glycerol, polyethylene glycol, etc. The suspension-assisting agents include, for example, casein, gelatin, alginic acid, carboxymethyl cellulose, gum arabic, hydroxypropyl cellulose, bentonire, etc. The preservatives include, for example, salicylic acid, ethyl p-oxybenzoate, propyl p-oxybenzoate, butyl p-oxybenzoate, etc.

The propellants include, for example, dimethyl ether, chlorofluorocarbon, carbon dioxide gas, LPG, etc. The film-forming agents include cellulose derivatives such as nitrocellulose, acetylcellulose, acetylbutyrylcellulose, methyl cellulose, etc.; vinyl resins such as vinyl acetate resins, etc.; polyvinyl alcohol; and silicones such as methyl polysiloxane, octamethyl cyclotetrasiloxane, decamethyl cyclopentasiloxane, dimethyl polysiloxane, methylphenyl polysiloxane, methyl polycyclopolysiloxane, dimethyl siloxane-methyl(polyoxyethylene)siloxane copolymers, dimethyl siloxane-methyl(polyoxyethylene-polyoxypropylene)siloxane copolymers, trimethyl siloxysilicate, octamethyl cyclotetrasiloxane silicone polyether polymers, etc.

The carrier used in formulating the present composition into a cream includes, for example, hydrocarbons such as paraffin, liquid paraffin, vaseline, etc.; silicon compounds such as dimethylsiloxane, colloidal silica, etc.; clay minerals such as bentonite, etc.; alcohols such as ethanol, stearyl alcohol, lauryl alcohol, ethylene glycol, polyethylene glycol, glycerol, etc.; carboxylic acids such as lauric acid, stearic acid, etc.; esters such as beeswax, lanolin, etc. Further, the same auxiliaries for formulation as used in formulating into the liquid formulations may be added.

The present composition may also be used by firstly formulating it into microencapsulated formulations and then formulating the resulting formulations into lotions, aerosols, etc.

To the present composition may further be added optional arthropod repellents other than carane-3,4-diol, p-menthane-3,8-diol, phenothrin and permethrin, antioxidants and the like.

Such optional arthropod repellents include, for example, N,N-diethyl-m-toluamide (Deet), dimethyl phthalate, 2-ethyl-1,3-hexanediol, N-octylbicycloheptanedicarboximide, 2,3,4,5-bis($\Delta^2$-butylene)-tetrahydrofurfural, di-n-propyl isocinchomeronate, di-n-butyl succinate, diethylmandelic acid amide, 2-hydroxyethyl octyl sulfide, empenthrin and the like. The antioxidants include, for example, butylhydroxy-anisole, dibutylhydroxytoluene, tocopherol, γ-oxyzanol and the like.

The present composition is used for repelling arthropods by applying it, as it is, directly to skin and the like. It may however be possible to repel arthropods by covering exposed part of skin or clothing with a sheet-like, film-like, net-like or band-like material on which the present composition is supported by a treatment such as coating, impregnation, kneading, etc.

The materials on which the present composition can be supported include, for example, resins such as polyethylene, polypropylene, polyvinylidene chloride, polyester, vinylon, nylon, etc., synthetic fibers made of these polymers; animal and vegetable fibers such as silk, cotton, wool, etc.; inorganic fibers such as aluminum, etc., and the mixtures thereof. When the net-like materials are used, the smaller size of mesh of the net is more preferred. Generally, however, the net is sufficiently useful if it is of a size of about 16 mesh or less.

The total amount of the active ingredients, i.e. a monoterpenediol selected from carane-3,4-diol and p-menthane-3,8-diol and a pyrethroid compound selected from phenothrin and permethrin, contained in the present composition varies depending upon the form of formulations and method of application. Generally, however, the total amount of the active ingredients falls within the range of from 0.1 to 70 wt. %, preferably from 1 to 40 wt. %, based on the total weight of the formulations.

The present composition is applied so that the total amount of a monoterpenediol selected from carane-3,4-diol and p-menthane-3,8-diol and a pyrethroid compound selected from phenothrin and permethrin usually falls within the range of from 0.01 to 2 mg, preferably 0.05 to 1 mg, per unit surface area (1 cm$^2$) of the skin. Of course, the amount may be varied depending upon the form of formulations, method of application, the kind and density of target arthropods and the like, and it may properly be increased or decreased independent of the range described above.

The present invention will be illustrated more specifically with reference to the following formulation examples and test example, but it is not to be interpreted as being limited to these examples.

First, formulation examples will be shown. In the examples, part is by weight.

Formulation Example 1

Two parts of d-phenothrin and 10 parts of 1S,3S,4S,6R-carane-3,4-diol are dissolved in ethanol, and the total weight of the solution is made up to 35 parts with ethanol. The resulting solution is charged into an aerosol container. After attaching a valve to the aerosol container, 65 parts of LPG (a propellant) is charged into the container through the valve part under pressure to obtain an aerosol.

Formulation Example 2

To 2 parts of permethrin and 8 parts of 1S,3S,4S,6R-carane-3,4-diol are added 10 parts of stearic acid, 2 parts of cetyl alcohol, 1 part of lanolin, 2 parts of liquid paraffin and 62 parts of water. The mixture is well mixed and turned into solution by heating. Thereafter, 13 parts of heated glycerol is added to the solution, which is then well stirred to obtain a cream.

Formulation Example 3

A mixture of 6 parts of stearic acid, 0.5 part of lanolin and 6 parts of Tween 60 (polyoxyethylene sorbitan monostearate produced by ICI America) is heated to 80° C. The thus heated mixture is added to a mixture of 75 parts of water and 2.5 parts of salicylic acid which latter mixture is heated to 60° C. While stirring the resulting mixture, 2 parts of d-phenothrin and 6 parts of 1S,3S,4S,6R-carane-3,4-diol are added thereto to obtain a lotion.

Formulation Example 4

Two parts of d-phenothrin and 10 parts of p-menthane-3,8-diol are dissolved in ethanol, and the total weight of the solution is made up to 35 parts with ethanol. The resulting solution is charged into an aerosol container. After attaching a valve to the aerosol container, 65 parts of LPG (a propellant) is charged into the container through the valve part under pressure to obtain an aerosol.

Formulation Example 5

To 2 parts of permethrin and 8 parts of p-menthane-3,8-diol are added 10 parts of stearic acid, 2 parts of cetyl alcohol, 1 part of lanolin, 2 parts of liquid paraffin and 62 parts of water. The mixture is well mixed and turned into solution by heating. Thereafter, 13 parts of heated glycerol is added to the solution, which is then well stirred to obtain a cream.

Formulation Example 6

A mixture of 6 parts of stearic acid, 0.5 part of lanolin and 6 parts of Tween 60 (polyoxy-ethylene sorbitan monostearate produced by ICI America) is heated to 80° C. The thus heated mixture is added to a mixture of 75 parts of water and 2.5 parts of salicylic acid which latter mixture is heated to 60° C. While stirring the resulting mixture, 2 parts of d-phenothrin and 6 parts of p-menthane-3,8-diol are added thereto to obtain a lotion.

Next, it will be shown by a test example that the present composition is outstandingly useful for arthropod repellency.

Test Example

A subject was covered at the upper half of his forearm (a part between the elbow and the wrist) with a cotton cloth while leaving the lower half uncovered. His upper arm and hand were protected with a supporter and an operating glove, respectively. An ethanol solution of every test compound was uniformly applied to the uncovered part of the forearm so that the amount of the active ingredient(s) was 3 g per unit surface area (m$^2$) of the skin. Thereafter, the subject inserted his forearm for 3 minutes into a cage (50 cm×50 cm×50 cm) containing fifty females of *Anopheles albimanus* and the number of bites by insects was counted. If the insect did not bite the forearm in the 3 minutes, then the same test was repeated at 30 minutes, 1 hour, 2 hours, 3 hours, 4 hours, 5 hours and 6 hours after the application of the ethanol solution. If the insect bit the forearm, even once, the test was discontinued. Table 1 shows the results.

TABLE 1

| Test compound | Dosage (g/m$^2$) | Number of bites (the lapse of time (hr) after application) | | | | | | | Effective time (hr) |
|---|---|---|---|---|---|---|---|---|---|
| | | 0.5 | 1 | 2 | 3 | 4 | 5 | 6 | |
| 1S,3S,4S,6R-carane-3,4-diol/ d-phenothrin | 2.7/0.3 | 0 | 0 | 0 | 0 | 0 | 0 | 0 | >6 |
| 1S,3S,4S,6R-carane-3,4-diol/ permethrin | 2.85/0.15 | 0 | 0 | 0 | 0 | 0 | 0 | 0 | >6 |
| p-Menthane-3,8-diol/ d-phenothrin | 2.7/0.3 | 0 | 0 | 0 | 0 | 0 | 0 | 0 | >6 |

TABLE 1-continued

| Test compound | Dosage (g/m²) | 0.5 | 1 | 2 | 3 | 4 | 5 | 6 | Effective time (hr) |
|---|---|---|---|---|---|---|---|---|---|
| p-Menthane-3,8-diol/ permethrin | 2.85/0.15 | 0 | 0 | 0 | 0 | 0 | 0 | 0 | >6 |
| 1S,3S,4S,6R-carane-3,4-diol | 3.0 | 0 | 0 | 0 | 2 | | | | 2 |
| p-Menthane-3,8-diol | 3.0 | 0 | 0 | 0 | 3 | | | | 2 |
| d-Phenothrin | 3.0 | 8 | | | | | | | <0.5 |
| Permethrin | 3.0 | 3 | | | | | | | <0.5 |
| Deet | 3.0 | 0 | 3 | | | | | | 0.5 |

Note: p-Menthane-3,8-diol used in the above test example was obtained by ring-closure of (+)-citronellal in sulfuric acid at room temperature. It contains p-menthane-3,8-cis-diol and p-menthane-3,8-trans-diol in an approximate weight ratio of 5:2.

As shown in Table 1, the present composition is an arthropod repellent composition having an outstanding performance which can surely repel arthropod over a long period of time.

What is claimed is:

1. An arthropod repellent composition which comprises a monoterpenediol compound selected from the group consisting of carane-3,4-diol and p-menthane-3,8-diol and a pyrethroid compound selected from the group consisting of phenothrin and permethrin as active ingredients wherein the weight ratio of the monoterpenediol compound to the pyrethroid compound falls within the range of from 1:1 to 50:1.

2. An arthropod repellent composition according to claim 1, wherein the weight ratio of the monoterpenediol compound and the pyrethroid compound falls within the range of from 2:1 to 30:1.

3. An arthropod repellent composition according to claim 1, wherein the monoterpenediol compound is carane-3,4-diol.

4. An arthropod repellent composition according to claim 1, wherein the monoterpenediol compound is p-menthane-3,8-diol.

5. A method for repelling arthropod which comprises applying an effective amount of the arthropod repellent composition according to any one of claims 1 to 5 to skin.

6. An arthropod repellent composition according to claim 1, wherein the pyrethroid compound is phenothrin.

7. An arthropod repellent composition according to claim 1, wherein the pyrethroid compound is permethrin.

8. An arthropod repellent composition according to claim 1, wherein the monoterpenediol compound is carane-3,4-diol and the pyrethroid compound is phenothrin.

9. An arthropod repellent composition according to claim 1, wherein the monoterpenediol compound is carane-3,4-diol and the pyrethroid compound is permethrin.

10. An arthropod repellent composition according to claim 1, wherein the monoterpenediol compound is p-menthane-3,8-diol and the pyrethroid compound is phenothrin.

11. An arthropod repellent composition according to claim 1, wherein the monoterpenediol compound is p-menthane-3,8-diol and the pyrethroid compound is permethrin.

12. An arthropod repellent composition according to claim 3, wherein the weight ratio of the monoterpenediol compound to the pyrethroid compound falls within the range of from 2:1 to 30:1.

13. An arthropod repellent composition according to claim 4, wherein the weight ratio of the monoterpenediol compound to the pyrethroid compound falls within the range of from 2:1 to 30:1.

14. An arthropod repellent composition according to claim 6, wherein the weight ratio of the monoterpenediol compound to the pyrethroid compound falls within the range of from 2:1 to 30:1.

15. An arthropod repellent composition according to claim 7, wherein the weight ratio of the monoterpenediol compound to the pyrethroid compound falls within the range of from 2:1 to 30:1.

16. An arthropod repellent composition according to claim 8, wherein the weight ratio of the monoterpenediol compound to the pyrethroid compound falls within the range of from 2:1 to 30:1.

17. An arthropod repellent composition according to claim 9, wherein the weight ratio of the monoterpenediol compound to the pyrethroid compound falls within the range of from 2:1 to 30:1.

18. An arthropod repellent composition according to claim 10, wherein the weight ratio of the monoterpenediol compound to the pyrethroid compound falls within the range of from 2:1 to 30:1.

19. An arthropod repellent composition according to claim 11, wherein the weight ratio of the monoterpenediol compound to the pyrethroid compound falls within the range of from 2:1 to 30:1.

* * * * *